US008883751B2

(12) United States Patent
Park et al.

(10) Patent No.: US 8,883,751 B2
(45) Date of Patent: Nov. 11, 2014

(54) COMPOSITION CONTAINING MICRORNA-21 INHIBITOR FOR ENHANCING RADIATION SENSITIVITY

(75) Inventors: Jong Bae Park, Seoul (KR); Seung Hoon Lee, Seoul (KR); Hee Jin Kwak, Goyang-si (KR); Tae Hoon Kim, Seoul (KR); Heon Yoo, Seoul (KR); Donghee Lee, Goyang-si (KR); Eun Kyoung Park, Goyang-si (KR); Hea Jin Kim, Goyang-si (KR)

(73) Assignee: National Cancer Center, Goyang-si (KR)

( * ) Notice: Subject to any disclaimer, the term of this patent is extended or adjusted under 35 U.S.C. 154(b) by 407 days.

(21) Appl. No.: 12/599,735

(22) PCT Filed: Jul. 30, 2008

(86) PCT No.: PCT/KR2008/004431
§ 371 (c)(1),
(2), (4) Date: Aug. 23, 2010

(87) PCT Pub. No.: WO2010/010980
PCT Pub. Date: Jan. 28, 2010

(65) Prior Publication Data
US 2011/0021601 A1 Jan. 27, 2011

(30) Foreign Application Priority Data
Jul. 23, 2008 (KR) .................. 10-2008-0071891

(51) Int. Cl.
A61K 48/00 (2006.01)
C07H 21/02 (2006.01)
C07H 21/04 (2006.01)
(52) U.S. Cl.
USPC .................. 514/44; 536/23.1; 536/24.5
(58) Field of Classification Search
CPC ............. C12N 15/113; C12N 2310/14; C12N 15/111; C12Q 1/6886
See application file for complete search history.

(56) References Cited

U.S. PATENT DOCUMENTS
2006/0185027 A1  8/2006  Bartel et al.

FOREIGN PATENT DOCUMENTS
WO  WO 03/029459  *  4/2003  .................. 536/24.5

OTHER PUBLICATIONS

Corsten et al. (Cancer Res, 2007, 67(19), 8994-9000).*
Nash et al. (Journal Viral Hepat, Jul. 2005, 12(4), 346-356).*
GenBank Accession No. AF480502, "Homo sapiens microRNA miR-104 gene, complete sequence," dated May 1, 2002, retrieved from http://www.ncbi.nlm.nih.gov/nuccore/20378942?from=1&to=22, 1 page.
Blower et al., "MicroRNAs modulate the chemosensitivity of tumor cells" Mol. Cancer Ther. 7(1): 1-9, Jan. 2008.
Cho, "OncomiRs: the discovery and progress of microRNAs in cancers" Molecular Cancer 6(60): 7 pages, Sep. 25, 2007.
Meng et al., "Involvement of Human Micro-RNA in Growth and Response to Chemotherapy in Human Cholangiocarcinoma Cell Lines" Gastroenterology 130: 2113-2129, 2006.
Verghese et al., "Small is beautiful: microRNAs and breast cancer—where are we now?" Journal of Pathology 215: 214-221, 2008.
Zhu et al., "MicroRNA-21 Targets the Tumor Suppressor Gene Tropomyosin 1 (*TPM1*)" The Journal of Biological Chemistry 282(19): 14328-14336, May 11, 2007.
"RNAi-mediated Therapy Against Drug and Radiation Resistance: Ochiya T," *Jpn. J. Cancer Clin.* 54(2):67-69, 2003.
Amin et al., "MicroRNA Detection and Response to Ionizing Radiation in Human Cancer Cells," *International Journal of Radiation Oncology *Biology *Physics* 66(3), Supplement, p. S561, Nov. 1, 2006, Abstract #2632.

* cited by examiner

*Primary Examiner* — Amy Bowman
(74) *Attorney, Agent, or Firm* — Seed IP Law Group PLLC

(57) ABSTRACT

Disclosed is a radiation sensitivity-enhancing composition in which a microRNA-21 inhibitor acts as an active ingredient. The microRNA-21 inhibitor is an antisense nucleic acid molecule binding complementarily to microRNA-21. The composition can be administered to a patient in conjunction with irradiation. The inhibitor can act as a radiosensitizer, enhancing the therapeutic effect of such irradiation on cancer high in microRNA-21 expression level, particularly, glioma.

5 Claims, 4 Drawing Sheets a.

b.

a.

b.

COMPOSITION CONTAINING MICRORNA-21 INHIBITOR FOR ENHANCING RADIATION SENSITIVITY

CROSS REFERENCE TO RELATED APPLICATIONS

This application is a national stage application filed under 35 U.S.C. §371 of International Patent Application No. PCT/KR2008/004431 accorded an international filing date of Jul. 30, 2008, which claims the benefit of priority to Korea (KR) Patent Application Serial No. 10-2008-0071891, filed Jul. 23, 2008. All the aforementioned patent applications are herein incorporated by reference in their entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is 690156_402USPCa_SEQUENCE_LISTING.txt. The text file is 1 KB, was created on Feb. 7, 2012 and is being submitted electronically via EFS-Web.

TECHNICAL FIELD

The present invention relates to a radiation sensitivity-enhancing composition. More particularly, the present invention relates to a radiation sensitivity-enhancing composition comprising a microRNA-21 inhibitor which represses microRNA-21 activity by binding complementarily to microRNA-21. Also, the present invention is concerned with a method for enhancing the radiation sensitivity of cancers high in microRNA-21 expression level, especially glioma.

BACKGROUND ART

Typically, surgery, radiotherapy and chemotherapy are used alone or in combination in the treatment of cancer. Of these cancer therapies, radiotherapy is widely used over a yearly increasing number of cancer patients.

Radiotherapy is now essential for the treatment of various cancers, but the radiation resistance of cancer cells and the damage to normal tissues caused by high doses of radiation are the main causes of a lowered efficiency of radiotherapy. Studies have been conducted into drugs that enhance radiation sensitivity (hereinafter referred to as "radiation sensitivity enhancers") in order to increase the efficiency of radiotherapy. Most of the radiation sensitivity enhancers developed thus far are for anticancer agents, such as Taxol, cisplatin, etc.

Also, tirapazamine was known as a radiation sensitivity enhancer which has no anticancer activity, but is known to act on hypoxic tumor cells only. Further, it is not effectively delivered into the inside of tumor tissue due to the characteristic internal pressure of hypoxic tumors, resulting in a low effect on radiotherapy.

However, in combination with radiotherapy, the anticancer agents which enhance radiation sensitivity are limitedly used because they cause side effects, that is, inflammation around radiation-treated areas, gastroenteric trouble, nausea, vomiting, diarrhea, etc.

In particular, central nervous system cancer occurs from different cell lineages including glia, such as astrocytes and ologodendrocytes. Astrocytomas (astrocytic tumors) may be divided into a diffuse type and a localized type depending on interaction with adjacent microenvironments. Localized astrocytoma grows with a limitedly invasive potential and a marked border to the surrounding regions whereas diffuse astrocytoma shows a peritumoral margin and invasion into cells distal to the primary lesion irrespective of tumor grade. Per the WHO (World Health Organization) classification, diffuse astrocytoma may be classified as low-grade diffuse astrocytoma (Grade II), anaplastic astrocytoma (Grade III) and glioblastoma multiforme (Grade IV; GBM) in the order of increasing malignancy. All three grades of these diffuse astrocytomas are invasive. Particularly, GBM is more malignant than the other astrocytomas in terms of proliferation, necrosis and hypoxia, angiogenesis, invasion to the support structure of the brain, and recurrence rate, and metastasis. Therefore, various attempts have been made to enhance the efficiency of treatment of these cancers. However, chemotherapy alone is insufficient for treatment of astrocytoma. Radiotherapy is also problematic in that the cancer cells become resistant to radiation.

In addition, along with surgery and treatment with anticancer agents, as mentioned above, radiotherapy is one of the most widely used regimens for brain tumors. However, despite surgery, chemotherapy, radiotherapy or a combination of therapies (e.g. radiotherapy and chemotherapy, or surgery and radiotherapy), WHO-Grade IV GBM shows poor prognosis (recurrence), with a median survival time less than about one year and a five-year survival rate less than 5%. Of the therapies for brain tumor, radiotherapy works by damaging the DNA of cells, thus inhibiting the cell cycle (DNA damage checkpoint) or inducing apoptosis to remove abnormal cells. However, problems with radiotherapy are the inherent resistance of cancer cells to radiation and the increase of radiation-resistance, which may lead to recurrence of the cancer. Further, radiation-resistant cancer cells become resistant to anticancer agents.

Therefore, there is an imperative need for radiation sensitivity enhancers that make cancer cells of inherent radiation resistance sensitive to radiation and optimize radiotherapy with the fewest number of side effects.

MicroRNAs, which are small regulatory RNA molecules found in various cancers, are now suggested as new targets for the treatment of cancer. MicroRNAs negatively regulate their target mRNAs by degradation or translational repression, thus functioning as tumor suppressors or oncogenes. Recent studies have reported the microRNA let-7 as an important tool for enhancing cytotoxic anticancer treatment by virtue of the ability thereof to alter radiation response. Under this background, the present inventors have studied the development of radiation sensitivity enhancers with an emphasis on microRNAs playing an important role in the post-transcriptional regulation mechanism.

It is reported that microRNA-21 shows high expression levels in the GBM samples of almost all patients and is overexpressed in various cancers. This report suggests that microRNA-21 serves as an oncogene of various cancers. In addition, microRNA-21 is reported to be involved in the regulation of apoptosis, cell proliferation and cell migration in breast cancer cell lines, colorectal cancer cell lines and other cancer cell lines. However, neither relationship between microRNA-21 overexpression and radiation resistance nor the enhancement of radiation sensitivity by microRNA-21 have thus far been reported in prior art.

Leading to the present invention, intensive and thorough research into radiation sensitivity enhancers, conducted by the present inventors, resulted in the finding that the expression level of microRNA-21 is closed related with radiation resistance and that a microRNA-21 inhibitor effectively enhances the sensitivity of cancer cells to radiation.

DISCLOSURE

Technical Problem

It is therefore an object of the present invention to provide a radiation sensitivity-enhancing composition comprising a microRNA-21 inhibitor.

It is another object of the present invention to provide a method for enhancing the radiation sensitivity of cancer having a high microRNA-21 expression level.

It is a further object of the present invention to provide radiotherapy comprising administering the composition in conjunction with irradiation.

Technical Solution

In accordance with an aspect thereof, the present invention pertains to a composition for enhancing sensitivity to radiation, comprising a microRNA-21 inhibitor.

The term "microRNA-21 inhibitor", as used herein, is intended to refer to an agent that reduces the intracellular expression or activity of microRNA-21. In more detail, the agent acts on microRNA-21 directly or on an upregulator of microRNA-21 indirectly to reduce the expression of microRNA-21 at the transcription level, promote the degradation of expressed microRNA-21, or disrupt the activity of microRNA-21, thereby decreasing the expression level or activity of microRNA-21.

MicroRNAs are, for the most part, encoded by introns on chromosomes and transcribed as primary transcripts which are then processed to shorter structures, known as precursor microRNAs (pre-miRNAs), by Drosha in the cell nucleus. Following nuclear export under the mediation of exportin, these pre-miRNAs are further processed to mature, about 22 bp-long miRNAs in the cytoplasm by interaction with Dicer which are associated with RNA interference silencing complex (RISC) to do gene silencing functions (Nat Rev Mol Cell Biol 6, 376-385; 2005). Functioning to reduce the expression level of microRNA-21 or to repress the activity, the microRNA-21 inhibitor according to the present invention has a significant influence on the pathway mediated by microRNA-21.

As long as it shows inhibitory activity against microRNA-21, anything can be used as a microRNA-21 inhibitor in the present invention, without limitation. Typically useful are biological molecules, compounds or isolates from plants or animals which can be applied to cells using standard techniques well known in the art, such as nucleic acids or polypeptides. Examples of the microRNA-21 inhibitor useful in the present invention include antisense nucleic acid molecules complementary to microRNA-21 base sequences, and microRNA-21-specific siRNAs, RNA aptamers, and ribozymes with higher preference for antisense nucleic acid molecules complementary to microRNA-21.

The term "complementary", as used herein, is intended to refer to having the ability to match the corresponding bases of two different nucleotide sequences with each other, that is, to form Watson-Crick base pairing therebetween.

An antisense nucleic acid molecule complementary to a microRNA-21 base sequence binds complementarily to a single-stranded fragment of microRNA-21 within cells to decrease the processing efficiency of microRNA-21, thus repressing the expression and inhibiting the activity of microRNA-21. The microRNA-21 molecules useful in the present invention may exist in single- or double-stranded forms. Mature microRNA molecules are primarily in single-stranded forms while precursor microRNAs are partially self-complementary to form double-stranded structures (e.g., stem-loop structures). The antisense nucleic acid molecules of the present invention may be complementary to single-stranded fragments of precursor microRNAs or to mature microRNA molecules. The nucleotide sequences of the microRNA-21 that the microRNA-21 inhibitor of the present invention targets are publicly available by reference to the database of the National Institute of Health (NIH), GenBank and to miRBASE (http://microrna. sanger.ac.uk/), for example, human microRNA-21 (miRBASE (http://microrna. sanger.ac.uk/) ID: hsa-mir-21 (Accession Nos. MI0000077 (ID: hsa-mir-21) for the precursor form and MIMAT0000076 (ID: hsa-miR-21, SEQ ID NO. 2) for the mature form)).

As non-enzymatic nucleic acid compounds which bind to microRNA-21 through RNA-RNA, RNA-DNA or RNA-PNA (peptide nucleic acid) interaction to modulate the activity of microRNA-21, the antisense nucleic acid molecules of the present invention may be complementary to microRNA-21 such that their one consecutive sequence binds to a microRNA-21 base sequence or they may partially be self-complementary to form loop structures which bind to looped microRNA-21.

Also, the antisense nucleic acid molecules binding complementarily to microRNA-21 in accordance with the present invention are preferably in the form of anti-oligonucleotides, which, when introduced into cells, can repress the expression of microRNA-21, show resistance to endogenous nucleases, such as exonucleases and endonucleases, and are selectively modified into stable forms within cells.

In the context of this invention, the term "oligonucleotide" is intended to refer to an oligomer or polymer of nucleotide monomers composed of naturally occurring sugars, nucleobases and intersugar linkages as well as to a modified or substituted nucleotide oligomer having non-naturally occurring portions which function similarly. Such substituted oligomers are often preferred over native forms because of desirable properties such as, for example, enhanced cellular uptake and increased stability in the presence of nucleases, and may be selected in a manner well known in the art. The oligonucleotide may be substituted entirely or partially. In addition, the anti-oligonucleotides of the present invention may include modified oligomer mimetics such as peptide nucleic acids (PNA) and locked nucleic acids (LNA) to increase the affinity of an oligonucleotide for its target and provide tolerance for mismatches to the target sequence.

Also, examples of the anti-oligonucleotides useful in the present invention include native oligonucleotides, phosphorothioate oligodeoxyribonucleotide, phosphorodithioate oligodeoxyribonucleotide, methylphosphonate oligodeoxyribonucleotide, phosphoramidate oligodeoxyribonucleotide, H-phosphonate oligodeoxyribonucleotide, triester oligodeoxyribonucleotide, alpha-anomeric oligodeoxyribonucleotide, peptide nucleic acids, and modified oligonucleotides including artificial nucleic acids and nucleic acid-modified compounds, but are not limited thereto.

In addition, the anti-oligonucleotides of the present invention are complementary to single-stranded base sequences of microRNA-21 and may include double- or single-stranded DNA, double- or single-stranded RNA, DNA/RNA hybrids, DNA and RNA analogs, and oligonucleotides with modifications of bases, sugars or backbones. The oligonucleotides of the present invention may be modified using well-known techniques in such a manner as to increase stability and resistance in the presence of nucleases. Modifications may be, as is known in the art, found in oligonucleotide backbones, sugar moieties, or bases, but is not limited thereto. The modifications in the ribonucleotide are generally at the 2' position of the ribose moiety with an —O-lower alkyl group containing 1-6 saturated or unsaturated carbon atoms, or with an —O-aryl or allyl group having 2-6 carbon atoms, wherein such —O-alkyl, aryl or allyl groups may be substituted or unsubstituted, e.g., with amino or halo groups (e.g., halo, hydroxy, trifluoromethyl, cyano, nitro, acyl, acyloxy, alkoxy, carboxyl, carbalkoxyl or amino groups). The oligonucleotides of the present invention, as illustrative and non-limiting examples, have at least four or five consecutive 2'-O-alkylated ribonucleotides at either or both of 3' and 5' terminal regions. Examples of 2'-O-alkylated groups include 2'-O-methyl, 2'-O-ethyl, 2'-O-propyl and 2'-O-butyl, but are not limited thereto.

The antisense nucleic acid molecules complementary to base sequences of microRNA-21 in accordance with the present invention may be isolated or prepared using standard molecular biological techniques, e.g., chemical synthesis or recombination, or may be commercially available. The antioligonucleotide of the present invention is preferably 15 to 40 nt in length and is more preferably composed of the base sequence of SEQ ID NO. 1.

On the other hand, the antisense nucleic acid molecules of the present invention, complementary to the microRNA-21 base sequences, may be provided in the form of an expression vector for delivery into cells.

The antisense nucleic acid molecules of the present invention can be introduced into cells using various transfection techniques including DEAE-dextran-, nucleoprotein- or liposome-mediated DNA transfection. In this regard, the antisense nucleic acid molecules may be anchored at a carrier allowing for the effective delivery thereof into cells. Preferably, the carrier is a vector, whether viral or non-viral. Examples of viral vectors useful in the present invention include vectors derived from lentivirus, retrovirus, adenovirus, herpes virus and avipox virus, preferably lentivirus, but are not limited thereto. Lentivirus, a kind of retrovirus, can productively infect both dividing and non-dividing cells because its pre-integration complex (virus "shell") can get through the nucleopores or intact membrane of the nucleus of the target cell.

The introduction of the antisense nucleic acid molecules of the present invention into cells causes the cancer cells to increase in radiation sensitivity. In this context, the term "introduction" is intended to mean the delivery of foreign DNA into cells through transfection or transduction. Transfection can be carried out using various methods well known in the art, including calcium phosphate-DNA co-precipitation, DEAE-dextran-mediated transfection, polybrene-mediated transfection, electroporation, microinjection, liposome fusion, Lipofectamine transfection, and protoplast fusion. Transduction refers to a process whereby foreign DNA is transferred to another cell via a virus or a viral vector particle on the basis of infection.

The microRNA-21 inhibitors useful in the present invention include microRNA-21-specific siRNA, RNA aptamers and ribozymes.

In the present invention, the siRNA useful as a microRNA-21 inhibitor means a duplex RNA which specifically cleaves microRNA-21 molecules to induce RNA interference (RNAi). Preferably, the siRNA of the present invention has a nucleotide sequence composed of a sense RNA strand homologous entirely or partially to a microRNA-21 nucleic acid sequence and an antisense RNA strand complementary thereto, which hybridizes with microRNA-21 within cells.

For use as a microRNA-21 inhibitor in the present invention, the RNA aptamer refers to a nucleic acid ligand which can adopt a specific three-dimensional conformation suitable for binding to microRNA-21 to form a complex therewith, showing an antagonist effect thereon. Typically, the aptamer may be a short nucleic acid molecule 15-50 nt in length which is folded into a predetermined secondary or tertiary structure, e.g., a stem-loop structure. Preferably, aptamers bind at a kd less than $10^{-6}$, $10^{-8}$, $10^{-10}$, or $10^{-12}$ to target molecules. The specificity of the aptamer for target molecules may be very high. Further, the aptamer may consist of a number of ribonucleotide units, deoxyribonucleotide units or a mixture of the two nucleotide units. Also, the aptamer may further comprise one or more modified base, sugar or phosphate backbone units.

A ribozyme, useful as a microRNA-21 inhibitor in the present invention, is an RNA molecule that catalyzes an intramolecular or intermolecular chemical reaction. Not only nucleases based on ribozymes found in the natural system, but also different types of ribozymes which catalyze similarly to nucleic acid polymerases, such as hammerhead ribozymes, hairpin ribozymes and tetrahymena ribozymes, are also useful in the present invention. Further, although not found in the natural system, the ribozymes engineered to catalyze specific reactions within the cells may also be employed. Ribozymes may cleave RNA or DNA substrates, with a preference for RNA substrates. Typically, a ribozyme recognizes, binds to and then cleaves a target substrate. The recognition is based on base pairing interaction therebetween, allowing for target-specific cleavage.

As used herein, the term "radiation sensitivity enhancement" is intended to refer to making cells more sensitive to radiation, thus enhancing the therapeutic efficiency of radiotherapy. Particularly, when applied to the radiotherapy of cancer cells, the radiation sensitivity enhancer ensures an increased death of cancer cells and an increase in the inhibition of the growth of cancer cells.

Showing inhibitory activity against microRNA-21 by, e.g., decreasing the expression level of microRNA-21 in cells, the microRNA-21 inhibitor of the present invention reduces the resistance of cells to radiation, that is, enhances the sensitivity of cells to radiation. The composition for enhancing radiation sensitivity comprising a microRNA-21 inhibitor in accordance with the present invention can target any cell to which radiotherapy can be applied, and is preferably useful in the enhancement of the radiation sensitivity of cancer cells.

As a matter of course, the composition for enhancing radiation sensitivity in accordance with the present invention can be applied to all of the cancer cells which are increased in radiation resistance by the expression of microRNA-21. It may be applied to the gene therapy of cancer cells with high expression levels of microRNA-21 preferably including glioma, breast cancer, lung cancer, colorectal cancer, prostate cancer, pancreatic cancer, uterine cancer, stomach cancer, and chronic lymphocytic leukemia, and more preferably to glioma, but are not limited thereto.

In addition, the composition comprising the microRNA-21 inhibitor in accordance with the present invention can increase radiation sensitivity through cell cycle regulation.

Having cell cycle regulating activity of arresting cells in $G_2/M$ phase, the microRNA-21 inhibitor of the present invention can render the cells more sensitive to radiation. Eukaryotic cells proliferate through the cell cycle consisting of four distinct phases $G_1$ phase, S phase (DNA synthesis), $G_2$ phase and M phase (mitosis). The first phase within interphase, from the end of the previous M phase until the beginning of DNA synthesis is called $G_1$ phase. In G1 phase, which is longer than the other phases, cells show the highest metabolic activity. In response to external signals, normal cells proceed from G1 phase to S phase and then G2 phase, followed by mitosis and cell division. In the absence of external signals, normal cells enter a state of quiescence called $G_0$ phase, a resting phase where the cell has left the cycle and stopped dividing. In contrast, cancer cells continue to proliferate with incessant DNA synthesis and mitosis according to the cell cycle irrespective of external signals. The regulation of the cell cycle thus leads to the inhibition of cancer cell growth. Thank to the ability thereof to arrest the cell cycle, the microRNA-21 inhibitor of the present invention can markedly enhance the cells' arresting effect provided by radiation.

In an embodiment of the present invention, the relationship between microRNA-21 expression and radiation resistance was examined by analyzing the expression level of mircroRNA-21 in radiation resistant cell lines such as RRC7 derived from U251 cell line, GBM cell lines including U373 and U87, and LN18. Compared to the parent cell line U251, RRC7 was observed to increase 1.6 times in miroRNA-21 expression level. As for GBM, the expression levels of microRNA-21 in U373 and U87 were measured to be 4.7 times and twice as large as that of the normal cell astrocytes. In contrast, the LN-18 cell line was 0.3 times reduced in microRNA-21 level compared to astrocytes (FIG. 1).

On the other hand, the correlation of microRNA-21 expression level with radiation resistance was proved by determining radiation resistance of the radiation-resistant cell lines RRC7, U373, U87 and LN18 through a colongenic assay. In this context, cancer cell lines with high microRNA-21 expression levels, such as breast cancer cell lines, lung cancer cell lines and uterine cancer cell lines, were analyzed for radiation resistance. RRC7 was found to be more resistant to radiation than was the parent cell line as measured by a colongenic assay. In addition, the GBM cell lines U373 and U87, both high in microRNA-21 expression level, were observed to show high resistance to radiation while low radiation resistance was measured in the glioblastoma LN18, which expresses microRNA-21 at a low level, implying that the expression of microRNA-21 correlates with radiation resistance (FIG. 2).

Further, in order to examine whether the cell cycle can be regulated by the overexpression of microRNA-21, the U373 cell line was exposed to radiation under the repression of the inherent microRNA-21 function with an anti-microRNA-21. The anti-microRNA-21-treated group was found to enhance the cell arrest in $G_2$/M phase of radiation, as compared to the control into which an anti-microRNA-negative control was transduced (FIG. 3).

Also, on the basis of the correlation between microRNA-21 overexpression and radiation resistance, an examination was made of whether the suppression of microRNA-21 by overexpressing anti-microRNA-21 leads to an increased sensitivity to radiation. In detail, 24 hours after transduction with anti-mir-21, U373, a GBM cell line high in microRNA-21 expression level, was exposed to radiation doses of 0, 1, 2, and 4 Gy. The cell line was cultured for two weeks with the culture medium substituted with a fresh one every two days. The group in which microRNA-21 was inhibited by treatment with anti-mir-21 and by exposure to radiation was found to markedly increase in radiation sensitivity compared to the control (FIG. 4).

The results obtained in the experiments imply that the microRNA-21 inhibitor represses the activity of microRNA-21 within cells, thus making the cells more sensitive to radiation.

In an embodiment, the composition for enhancing radiation sensitivity comprising a microRNA-21 inhibitor in accordance with the present invention may further comprise and be formulated with a pharmaceutically acceptable vehicle.

The term "pharmaceutically acceptable vehicle", as used herein, is intended to refer to a carrier or a diluent which does not destroy the pharmaceutical activities and properties of the ingredient and which does not irritate the subject to be treated. For use in liquid formulations of the composition of the present invention, the pharmaceutically acceptable vehicle is preferably suitable for sterilization. The active ingredient of the present invention may be formulated with one selected from among saline, sterile water, Ringer's solution, buffered saline, albumin injection, dextrose solution, maltodextrose solution, glycerol, ethanol and combinations thereof, and if necessary, in combination with other conventional additives including antioxidants, buffer, bacteriostatic agents, etc. Alternatively, the composition of the present invention may be formulated into injections, pills, capsules, granules, or tablets with diluents, dispersants, surfactants, binders and lubricants.

The composition comprising a microRNA-21 inhibitor and a pharmaceutically acceptable vehicle in accordance with the present invention may be formulated into any dosage form, whether oral or non-oral and may be in unit dosage form for the convenience of administration and the uniformity of administration amounts. The pharmaceutical formulations according to the present invention may be administered via oral, rectal, nasal, topical (bolus and sublingual), transdermal, vaginal, or parenteral (intramuscular, subcutaneous, intravenous) routes or by inhalation or insufflation.

Examples of the oral dosage forms formulated with the composition of the present invention include tablets, troches, lozenges, water-soluble or oil suspensions, powders or granules, emulsions, hard or soft capsules, syrups and elixirs. For tablet or capsule formulations, useful are additives including a binder, such as lactose, saccharose, sorbitol, mannitol, starch, amylopectin, cellulose or gelatin, an excipent such as dicalcium phosphate, a disintegrant such as corn starch or sweet potato starch, and a lubricant, such as magnesium stearate, calcium stearate, sodium stearyl fumarate, or polyethylene glycol. In addition to these additives, a liquid carrier such as fat oil may be used for capsule formulations.

For use in parenteral administration, the composition of the present invention may be formulated into injections via subcutaneous, intravenous or intramuscular routes, suppositories, or sprays via inhalation, such as aerosols. Injections may be prepared by mixing the composition of the present invention with a stabilizer or buffer in water to give solutions or suspensions which are packaged in unit dosages such as ampules or vials. For suppositories, the composition of the present invention may be formulated with a conventional base such as cocoa butter or other glycerides, or an enema. The composition of the present invention in the form of a water-dispersed concentrate or a wet powder may be formulated with a propellant to prepare an aerosol spray.

In accordance with another aspect thereof, the present invention pertains to a method for making cancer cells sensitive to radiation using the radiation sensitivity enhancing composition comprising a microRNA-21 inhibitor. Also, the present invention addresses radiotherapy for cancer cells comprising the administration of the composition of the present invention.

The term "administration", as used herein, is intended to mean the introduction of the pharmaceutical composition of the present invention to a subject using any appropriate method, as exemplified by the delivery of the microRNA-21 inhibitor, e.g., an antisense nucleic acid molecule, using viral or non-viral technology. When introduced into cancer cells, the composition of the present invention reduces the expression level or activity of microRNA-21 thus enhancing the sensitivity of the cells to radiation.

As long as it ensures the arrival of the composition of the present invention to a tissue of interest, any route may be taken for administration. For example, the composition of the present invention may be administered orally, rectally, topically, intravenously, intraperitoneally, intramuscularly, intraarterially, transdermally, intranasally, intrathoracically, intraocularly, or intradermally. Preferably, the anticancer composition of the present invention may be administered locally into cancer tissue.

Radiation therapy for cancer in accordance with the present invention includes administering the radiation sensitivity enhancing composition of the present invention in a pharmaceutically effective amount. In this context, the term "therapeutically effective amount" means an amount in which the tumor cells become effectively sensitive to radiation. It will be apparent to those skilled in the art that the suitable total daily dose may be determined by an attending physician within the scope of sound medical judgment. The specific therapeutically effective dose level for any particular patient may vary depending on a variety of factors, including the kind and degree of desired reaction, the specific composition, including the use of any other agents according to the intended use, the patient's age, weight, general health, gender, and diet, the time of administration, route of administration, and rate of the excretion of the composition; the duration of the treatment and the amount of the irradiation; other drugs used in combination or coincidentally with the specific composition; and similar factors well known in the medical arts. Accordingly, the effective amount of the radiation sensitivity enhancing composition suitable for the purpose of the present invention is preferably determined in full consideration of the above-mentioned factors. In some cases, the radiation sensitivity enhancing composition of the present invention may also be administered in conjunction with irradiation; such treatment may be especially beneficial as the microRNA-21 inhibitor can act as an enhancer of radiation sensitivity, enhancing the therapeutic effect of such irradiation.

Further, the radiation therapy in accordance with the present invention may be applied to any animal that increases in radiation resistance with increasing of microRNA-21 expression level. Examples of the animal include cows, pigs, sheep, horses, dogs and cats as well as humans and primates. The radiation therapy in accordance with the present invention may be also applied to any cancer featuring radiation resistance resulting from the expression of microRNA-21, and preferably to cancers with high microRNA-21 expression levels, including glioma, breast cancer, lung cancer, colorectal cancer, prostate cancer, pancreatic cancer, uterine cancer, stomach cancer, and chronic lymphocytic leukemia, but is not limited thereto.

As used herein, the term "radiation therapy" or "radiotherapy" is intended to include administering cancer cells with the composition of the present invention and exposing the cancer cells to radiation. Irradiation means ionizing radiation and in particular gamma radiation, especially that emitted by linear accelerators or by the radionuclides that are in common use today. The irradiation of the tumor by radionuclides can be external or internal. Preferably, the administration of the composition of the present invention commences up to one month, in particular up to 10 days or a week, before the irradiation of the tumor. Additionally, it is advantageous to fractionate the irradiation of the tumor and maintain the composition administration in the interval between the first and the last irradiation sessions. The amount of the composition, the dose of irradiation and the intermittence of the irradiation doses will depend on a series of parameters such as the type of tumor, its location, the patients' reaction to chemo- or radiotherapy. Also, brachytherapy, radionuclide therapy, external beam radiation therapy, thermotherapy (cryoblation, hyperthermal therapy), radiation surgery, charged-particle radiotherapy, neutron radiotherapy, and photodynamic therapy may be included within the scope of the radiotherapy useful in the present invention.

Advantageous Effects

When used in conjunction with irradiation, the radiation sensitivity-enhancing composition comprising a microRNA-21 inhibitor according to the present invention can enhance the therapeutic effect of radiotherapy for various cancers which are resistant to radiation.

MODE FOR INVENTION

Figure 1:
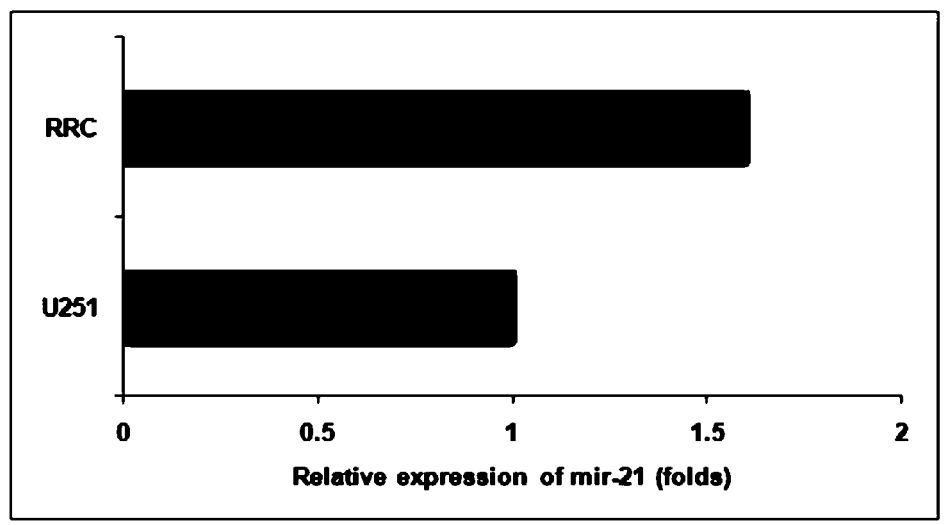
FIG. 1a is graph showing relative expression levels of microRNA-21 in the radiation resistant cell clone RRC7 and the parent cell line U251 and FIG. 1b is a graph showing relative expression levels of microRNA-21 in brain tumor cell lines U87, U373 and LN 18.
Figure 1:
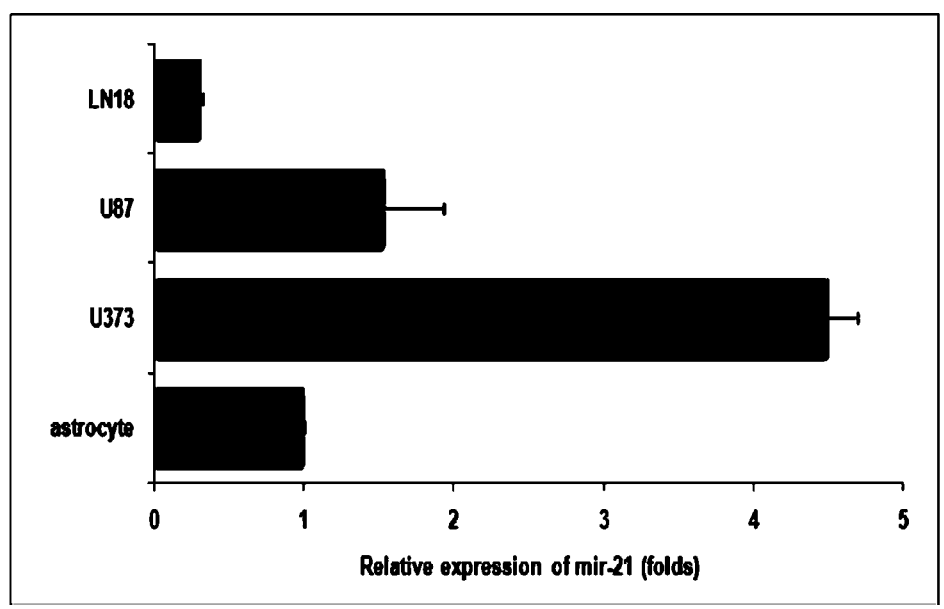

A better understanding of the present invention may be obtained through the following examples which are set forth to illustrate, but are not to be construed as limiting the present invention.

EXAMPLE 1

Establishment of Radiation-Resistant Cell

Clone and microRNA-21 Expression Level in Brain Tumor Cells

<1-1> Cell Culture

Cells were cultured as follows.

(1) The brain tumor cell lines U87, U373, LN-18, and U251 were cultured in DMEM (WelGENE, Korea, or GIBCO BRL, U.S.A.) supplemented with 10% FBS (fetal bovine serum, Gibco BRL, U.S.A.) and 100 units/ml penicillin and 100 μg/ml streptomycin under a wet atmosphere in a 37° C., 5% $CO_2$ incubator.

(2) The breast cancer cell lines MCF7 and MB-MDA-231 were cultured in DMEM (WelGENE, Korea) supplemented with 10% FBS (fetal bovine serum, Gibco BRL, U.S.A.) and containing 100 units/ml penicillin and 100 μg/ml streptomycin under a humidified atmosphere in a 37° C., 5% $CO_2$ incubator.

(3) The lung cancer cell line A549 was cultured in a RPMI 1640 (WelGENE, Korea) medium supplemented with 10% FBS (fetal bovine serum, Gibco BRL, U.S.A.) 100 units/ml penicillin and 100 μg/ml streptomycin under a humidified atmosphere in a 37° C., 5% $CO_2$ incubator.

<1-2> Establishment of Radiation-Resistant Cell Clone

In order to establish radiation-resistant cell clones, the U251 glioblastoma multiforme (GBM) cell line was exposed to radiation and cultured to form colonies. In greater detail, when grown at 70~80% confluence, the U251 cells were irradiated at room temperature every three days with the radiation from a $^{137}Cs$ gamma-ray source at a dose of 3 Gy using a Gammacell Elite irradiator (dose rate: 3 Gy/min). Cell colonies which were alive after every-third-day-exposure to 3 Gy of gamma radiation during 6 months were collected and grown to a predetermined population on culture dishes. The radiation-resistant cell strain thus obtained was named RRC7.

<1-3> Expression Levels of microRNA-21 in Tumor Cell Lines and Radiation-Resistant Cell Clone (RRC7)

An examination was made of whether the expression level of microRNA-21 is associated with radiation resistance by analyzing the radiation-resistant cell clone (RRC7) and brain tumor cell lines for microRNA-21 expression level through real-time PCR.

In addition, an examination was made of whether the expression level of microRNA-21 is difference between the normal cells and the brain tumor cells by analyzing the normal cells astrocytes and the brain tumor cell lines U87, U373 and LN18 for microRNA-21 expression level through real-time PCR.

In greater detail, when the cells grew at 70-80% confluence on 6-well plates, the culture medium was removed, followed by washing the cells twice with DBPS. Total RNA was isolated using TRI reagent (Invitrogen, U.S.A.) as follows. First, in order to extract total RNA from nucleoprotein complexes, cells were treated with 1 ml of TRI reagent and incubated for 5 min at room temperature. Then, 0.2 ml of chloroform was added to the cells per 1 ml of TRI reagent and vigorously shaken for 15 sec with the hand before incubation for 3 min at room temperature. Centrifugation at 4° C. at 12,000×g for 15 min gave a total RNA layer. The total RNA layer thus obtained was mixed with 0.5 ml of isopropanol and centrifuged at 4° C. at 12,000×g for 10 min to afford a total RNA pellet which was then washed with 75% EtOH. After removal of 75% EtOH, the pellet was dried and dissolved in DEPC-$H_2O$. The total RNA was quantitatively and qualitatively analyzed using a spectrophotometer. The total RNA was diluted to a concentration of 25 ng/μl before real-time PCR in which mirVana™ qRT-PCR miRNA Detection Kit (Ambion, U.S.A.) was used to quantify expression levels of mature microRNA-21. Starting with denaturation at 95° C. for 10 min, PCR was performed with 40 cycles including at 95° C. for 15 sec and at 60° C. for 60 sec, under monitoring with an ABI 7500 real time PCR system.

The radiation resistant cell clone RRC7 was 1.6 times as large in microRNA-21 expression level as the parent cell line U251 (FIG. 1a). The tumor cell lines U87 and U373 were found to respectively overexpress microRNA-21 at a level increased by 1.5 to 4.5 times over that of normal astrocytes. In contrast, the expression level of microRNA-21 in LN18 was 0.3-fold reduced (FIG. 1b).

EXAMPLE 2

Radiation Resistance According to Expression Level of microRNA-21

In order to examine the correlation of radiation resistance with microRNA-21 expression level, the radiation resistant cell line RRC7 and the brain tumor cell lines U251, U373, U87 and LN18 were analyzed for radiation resistance using a colongenic assay.

Radiation resistance was measured in high microRNA-21 level breast cancer cell lines, lung cancer cell lines and uterine cancer cell lines as well.

The clonogenic assay was performed as follows. The radiation-resistant cell line RRC7, the brain tumor cell lines U251, U373, U87 and LN18, the breast cancer cell lines MCF-7 and MB-MDA-231, the lung cancer cell line A549 and the uterine cancer cell line HeLa, all in the log-phase, were harvested and suspended in fresh cell culture media. Each suspension was inoculated in triplicate at a density of 100 cells per dish into 60-mm culture dishes. 24 hours after inoculation, the cells were exposed to radiation. Gamma radiation was irradiated into U373, U87 and LN18 (brain tumor cell lines), MCF-7 and MB-MDA-231 (breast cancer cell lines), A549 (lung cancer cell line), and HeLa (uterine cancer cell line) at doses of 0 Gy (control), 2 Gy, 4 Gy and 8 Gy (experimental groups). RRC7 and U251 were exposed at doses of 0 Gy (control), 3Gy, 6Gy and 9Gy (experimental groups). After irradiation, the cells were cultured for 2 weeks with the provision of a fresh culture medium every other day. For colony identification, the cells were stained with a Diff-quik solution (Sysmex, Japan) and colonies composed of 50 or more cells were counted.

As a result, higher inherent expression levels of microRNA-21 were categorically linked to higher radiation resistance. The radiation-resistant cell clone RRC7 was also found to show higher radiation resistance than did the U251 brain tumor cell line (FIG. 2a).

Figure 2:
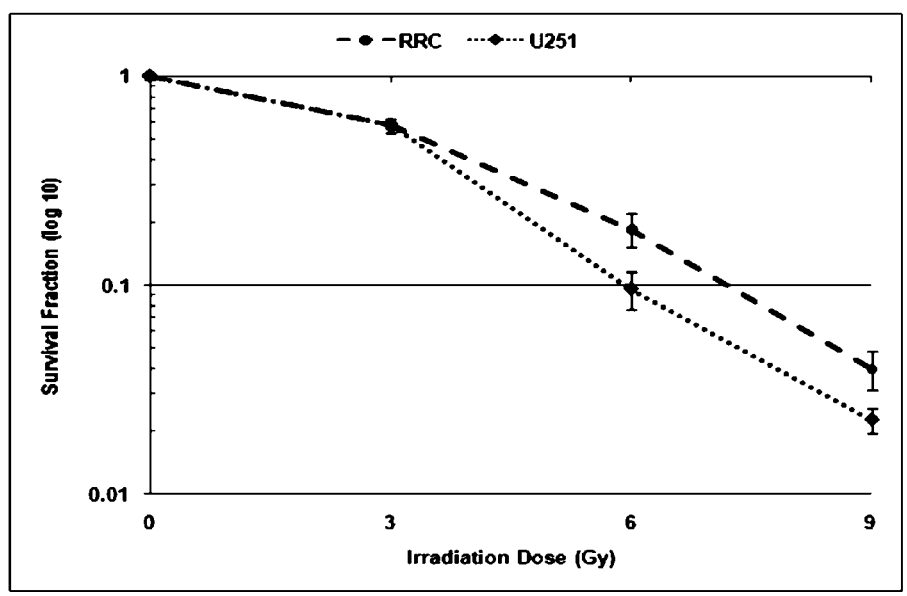
FIG. 2 shows graphs in which survival fractions are plotted against irradiation doses for the radiation resistant cell clone RRC7 and the parent cell line U251 (a) and for U373, U87, LN18 (brain tumor cell lines), MCF-7 and MB-MDA-231 (breast cancer cell lines), A549 (lung cancer cell line), and HeLa (uterine cancer cell line) (b).
Figure 2:
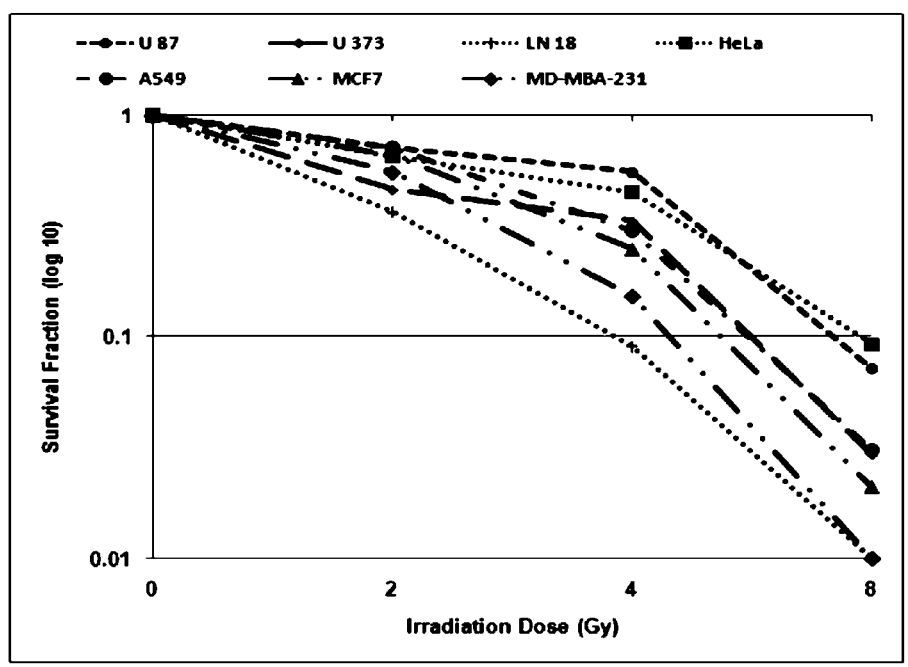

In addition, the brain tumor cell lines U373 and U87, both relatively high in microRNA-21 level, were observed to be more resistant to radiation than was the LN-18 cell line, relatively low in microRNA-21 level (FIG. 2b). Also, HeLa, A549 and MCF7 were observed to have radiation resistance similar to that of the brain tumor cell lines U373 and U87 (FIG. 2b).

Accordingly, the colonergic assay showed that the expression level of microRNA-21 is closely correlated with radiation resistance.

EXAMPLE 3

Use of Anti-Oligonucleotide Against MicroRNA-21 (Anti-Micro RNA-21) in Arresting Cells in G2/M Phase In order to examine whether the repression of microRNA-21 activity leads to an arrest of the cell cycle, U373, a brain tumor cell line with a high expression level of microRNA-21, was assayed for cell cycle after treatment with anti-microRNA-21 and radiation.

Anti-microRNA-21, complementary to microRNA-21, was transduced into cells to repress microRNA-21 activity. For reference, anti-microRNA-negative control (Dharmacon, U.S.A.) was used. Transduction was performed by electroporation using a Cell Line Nucleofector kit T solution (Amaxa, U.S.A.).

Cells were aliquoted into 15 ml conical tubes and centrifuged at 1,000 rpm for 5 min. The cells thus harvested were washed twice with DPBS and centrifuged at 90×g for 10 min. Thereafter, the cells were suspended in 100 μl of a T solution containing 100 nM of anti-microRNA-21, followed by electroporation using an Amaxa electroporator. Immediately, the cells were suspended in 1 ml of DMEM supplemented with 10% FBS and then diluted to a population of $2 \times 10^5$ cells in DMEM supplemented with 10% FBS at 37° C. Each dilution was inoculated in triplicate into 60 mm culture dishes and incubated at 37° C. for 24 hours.

Cell cycles were measured as follows. After incubation for 24 hours, cells were irradiated at a dose of 8 Gy. Subsequently, the irradiated groups together with the control (0 Gy) were incubated for 24 hours in a cell culture incubator. Then, the cells were aliquoted into 15 ml conical tubes and centrifuged at 1,000 rpm for 5 min. The cells thus harvested were washed twice with DPBS and suspended in 500 µl of ice-cold DPBS. The cell suspension was added to 4.5 ml of ice-cold 70% EtOH and mixed with shaking. Incubation at 4° C. for 16 hours in a refrigerator allowed the cells to be fixed. Cells were centrifuged at 4° C. at 1,500 rpm for 15 min, and the cell pellets thus obtained were washed twice with ice-cold DPBS and suspended in 1 ml of PI solution (Propidium Iodide 100 µg/ml, DNase-free RNase 20 µg/ml, 0.1% Triton X-100) before incubation at 37° C. for 15 min. After centrifugation at 4° C. at 1,500 rpm for 15 min, the cell pellets were suspended in 1 ml of ice-cold DPBS. The cell suspensions were transferred into FACS tubes which were brought into FACS Calibur (BD science, U.S.A.) for cell cycle measurement.

Figure 3:
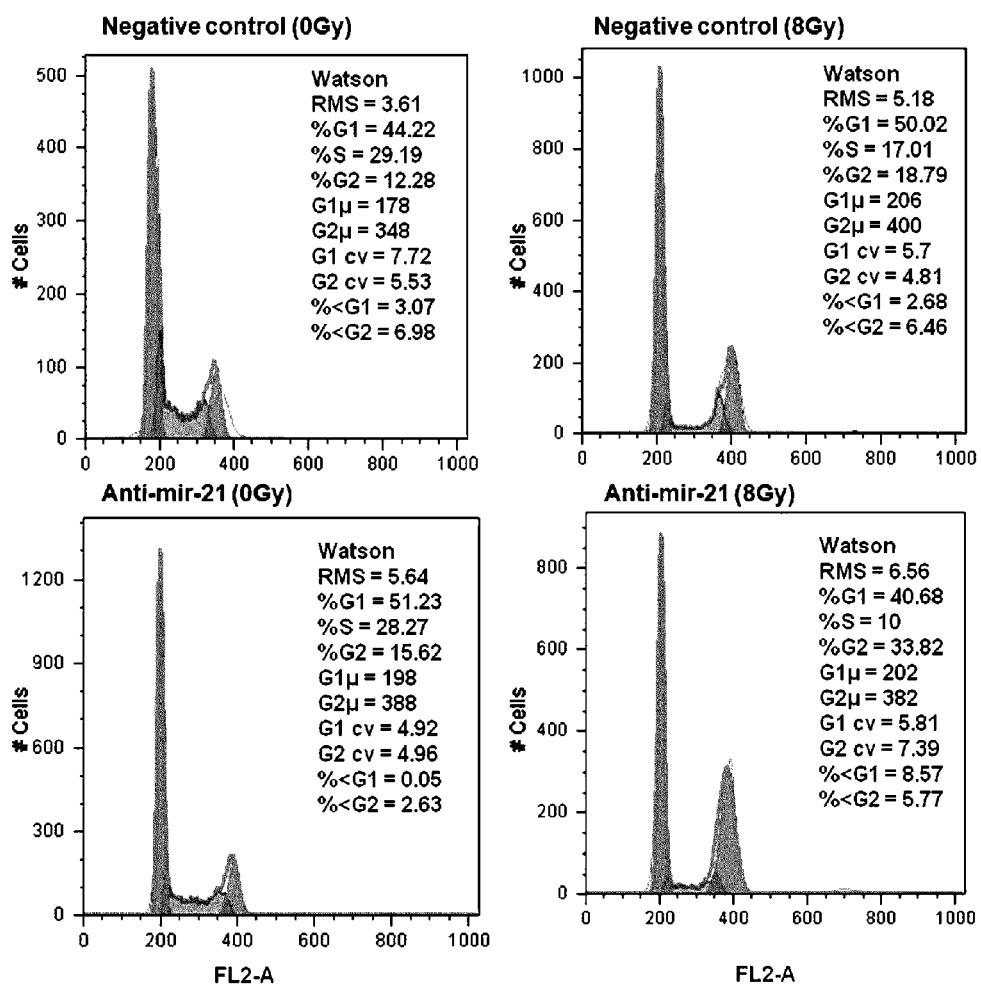
FIG. 3 is graphs showing the enhancement effect of anti-microRNA-21 on arrest in G2/M phase.

As a result, the U373 cell line was exposed to radiation under the repression of the inherent microRNA-21 function with an anti-microRNA-21. The anti-microRNA-21-treated group was found to enhance the cell arrest in $G_2$/M phase of radiation, as compared to the control into which an anti-microRNA-negative control was transduced (FIG. 3).

EXAMPLE 4

Use of Anti-Oligonucleotide Against MicroRNA-21 (Anti-MicroRNA-21) for Increasing Radiation Sensitivity In order to examine whether the repression of microRNA-21 activity leads to an increase in radiation sensitivity, U373 and U87, both brain tumor cell lines with high expression levels of microRNA-21, were assayed for radiation resistance after treatment with anti-microRNA-21 and radiation.

Anti-microRNA-21, complementary to microRNA-21, was transduced into cells to repress microRNA-21 activity. For reference, anti-microRNA-negative control (Dharmacon, U.S.A.) was used. Transduction was performed by electroporation using a Cell Line Nucleofector kit T solution (Amaxa, U.S.A.).

Cells were aliquoted into 15 ml conical tubes and centrifuged at 1,000 rpm for 5 min. The cells thus harvested were washed twice with DPBS and centrifuged at 90×g for 10 min. Thereafter, the cells were suspended in 100 µl of a T solution containing 100 nM of anti-microRNA-21, followed by electroporation using an Amaxa electroporator. Immediately, the cells were suspended in 1 ml of DMEM supplemented with 10% FBS and then diluted to a population of $1 \times 10^3$ cells in DMEM supplemented with 10% FBS at 37° C. Each dilution was inoculated in triplicate into 60 mm culture dishes and incubated at 37° C. for 24 hours.

After the transduction, U373 and U87 cells were irradiated at doses of 0 Gy, 1 Gy, 2 Gy and 4 Gy and cultured for two weeks with the substitution of culture medium with a fresh one every other day. For colony identification, the cells were stained with a Diff-quik solution (Sysmex, Japan) and colonies composed of 50 or more cells were counted.

Figure 4:
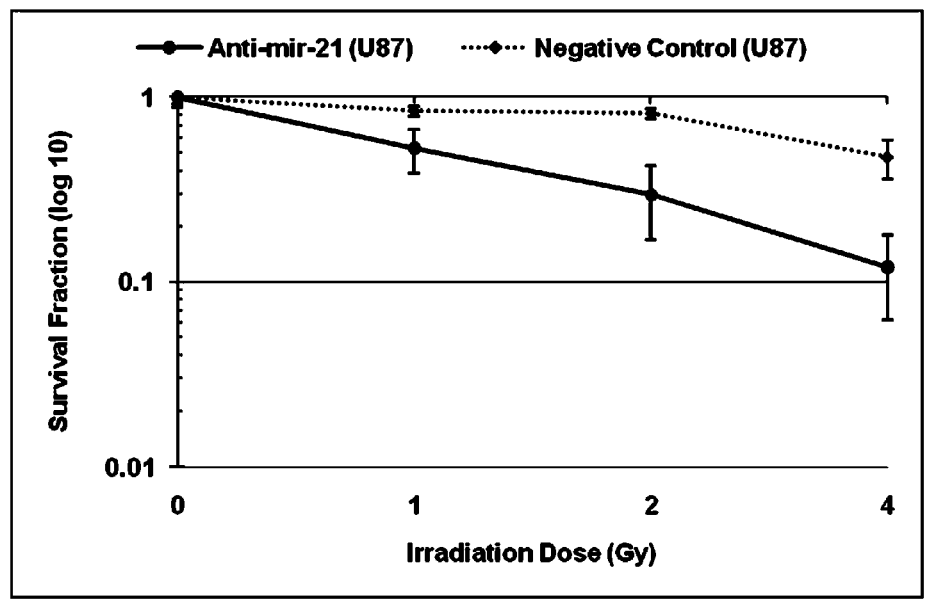
FIGS. 4a and 4b are graphs showing the enhancing effect of anti-microRNA-21 on radiation sensitivity.
Figure 4:
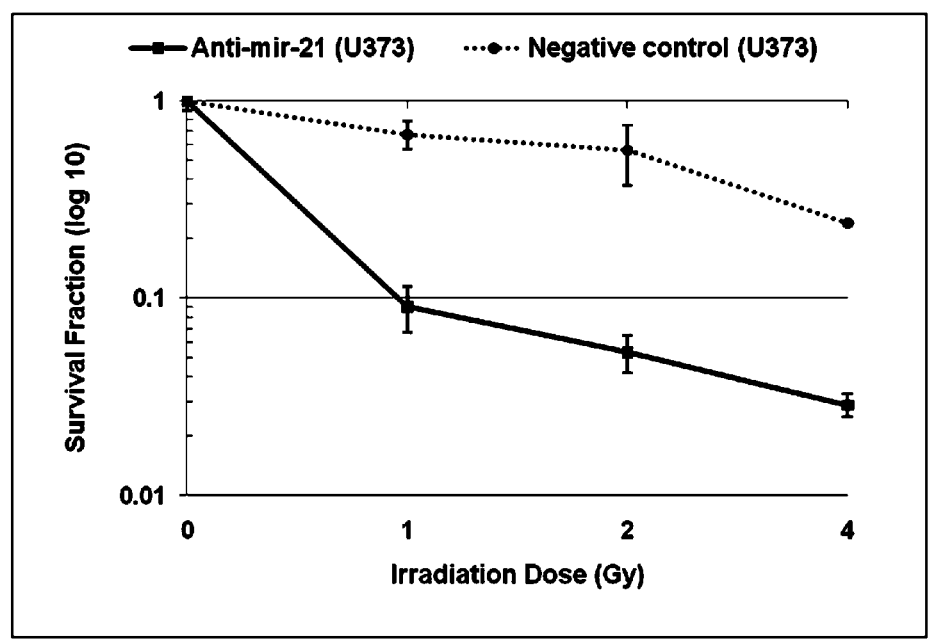

The experimental groups of U87 and U373 in which inherent microRNA-21 activity was repressed by treatment with anti-microRNA-21 were found to be more sensitive to radiation than were the cells transduced with anti-microRNA-negative control (FIGS. 4a and 4b).

Thus, the results showed the close correlation of microRNA-21 with radiation resistance, implying that anti-microRNA-21 can be used to make cells sensitive to radiation.

INDUSTRIAL APPLICABILITY

As described hitherto, the microRNA-21 inhibitors of the present invention, especially antisense nucleic acid molecules binding complementarily to microRNA-21, make cancer cells sensitive to radiation and show no side effects such as cytotoxicity.

Accordingly, the composition for enhancing radiation sensitivity, comprising the microRNA-21 inhibitor in accordance with the present invention is useful in radiotherapy of cancers which have become resistant to radiation due to a high expression level of microRNA-21 therein.

The invention claimed is:

1. A method of treating a cancer with radiotherapy, comprising (a) administering to an animal a therapeutically effective amount of a composition comprising a microRNA-21 inhibitor to enhance radiation sensitivity of the cancer, and (b) exposing the animal to radiation,
   wherein the cancer is (i) high in microRNA-21 expression level and radiation resistance, and (ii) selected from the group consisting of glioma, breast cancer, lung cancer, and uterine cancer, and
   wherein the microRNA-21 inhibitor is an antisense nucleic acid molecule comprising the nucleotide sequence set forth in SEQ ID NO: 1.

2. The method of claim 1, wherein the cancer is glioma.

3. The method of claim 1, wherein the antisense nucleic acid molecule is included in an expression vector for delivery into a cell.

4. The method of claim 3, wherein the expression vector is a viral vector derived from a virus selected from the group consisting of lentivirus, retrovirus, adenovirus, herpes virus, and avipox virus.

5. A method for increasing cell cycle arrest at the G2/M phase of a cell, said method comprising:
   (a) administering to an animal a therapeutically effective amount of a composition comprising a microRNA-21 inhibitor that is an oligonucleotide comprising the nucleotide sequence set forth in SEQ ID NO:1, and
   (b) exposing the animal to radiation,
   thereby increasing cell cycle arrest at the G2/M phase,
   wherein the animal has a cancer which is high in microRNA-21 expression level and radiation resistance,
   wherein the cancer is selected from the group consisting of glioma, breast cancer, lung cancer, and uterine cancer.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: Sequence of anti-microRNA 21 oligonucleotide

<400> SEQUENCE: 1
tcaacatcag tctgataagc ta                                              22

<210> SEQ ID NO 2
<211> LENGTH: 22
<212> TYPE: RNA
<213> ORGANISM: Artificial
<220> FEATURE:
<223> OTHER INFORMATION: Mature sequence of hsa-miR-21

<400> SEQUENCE: 2
uagcuuauca gacugauguu ga                                              22
```